US00PP27855P3

(12) United States Plant Patent
Klemm et al.

(10) Patent No.: US PP27,855 P3
(45) Date of Patent: Apr. 4, 2017

(54) ***PETUNIA* PLANT NAMED 'KLEPH15261'**

(50) Latin Name: *Petunia hybrida*
Varietal Denomination: KLEPH15261

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 151 days.

(21) Appl. No.: 14/545,758

(22) Filed: Jun. 15, 2015

(65) Prior Publication Data

US 2016/0366803 P1 Dec. 15, 2016

(51) Int. Cl.
*A01H 5/02* (2006.01)

(52) U.S. Cl.
USPC ..... Plt./356.1

(58) Field of Classification Search
USPC ..... Plt./263.1, 356.1
See application file for complete search history.

*Primary Examiner* — Susan McCormick Ewoldt
*Assistant Examiner* — Karen Redden
(74) *Attorney, Agent, or Firm* — James M. Weatherly; Bethany R. Roahrig; Cochran Freund & Young, LLC

(57) ABSTRACT

A new *petunia* plant particularly distinguished by having a yellow flower color with a uniform corolla, a medium vigor and a semi-trailing plant habit, is disclosed.

1 Drawing Sheet

Genus and species: *Petunia hybrida.*
Variety denomination: 'KLEPH15261'.

BACKGROUND OF THE NEW PLANT

The present invention comprises a new and distinct variety of *petunia*, botanically known as *Petunia hybrida* and hereinafter referred to by the variety name 'KLEPH15261'. 'KLEPH15261' is a selection from a cross-pollination of the proprietary female *petunia* line 'PH-2011-2754' (unpatented) and the proprietary male *petunia* line 'PH-2009-1258' (unpatented).

In July of 2011, the proprietary female *petunia* line 'PH-2011-2754' and the proprietary male *petunia* line 'PH-2009-1258' were cross pollinated in Latina, Italy and seeds were obtained. The seeds were sown and plants were grown for evaluation. A plant line was selected in April 2012 in Latina, Italy and named 'KLEPH15261'. In May 2012, 'KLEPH15261' was first vegetatively propagated by terminal tip cuttings and tissue culture in Latina, Italy. 'KLEPH15261' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Yellow flower color with a uniform corolla;
2. A medium vigor; and
3. A semi-trailing plant habit.

DESCRIPTION OF THE PHOTOGRAPH

This new *petunia* plant is illustrated by the accompanying photograph, which shows a close-up of the flower of the plant. The plant is about 3 months-old grown in Stuttgart, Germany in April 2014.

The colors shown are as true as can be reasonably obtained by conventional photographic procedures.

DESCRIPTION OF THE NEW VARIETY

The following detailed descriptions set forth the distinctive characteristics of 'KLEPH15261'. The data which define these characteristics were collected from asexual reproductions carried out in Latina, Italy. Data was collected on ten-week-old plants grown indoors in Latina, Italy under greenhouse conditions in February 2015. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH15261'.

Parentage:
- *Female.*—Proprietary *petunia* line 'PH-2011-2754'.
- *Male.*—Proprietary *petunia* line 'PH-2009-1258'.

Plant:
- *Form.*—Medium vigor.
- *Habit.*—Semi-trailing.
- *Height* (*from top of soil*).—About 7.0 cm.
- *Width* (*horizontal plant diameter*).—About 16.0 cm.
- *Propagation.*—Terminal tip cuttings.
- *Time to produce a finished flowering plant.*—About 13 weeks in winter under short day conditions, 7 weeks in spring.
- *Time to initiate and develop roots.*—2 to 3 weeks.
- *Root description.*—Moderate density, moderate branching, white roots.

Stems:
- *Average number* (*basal*).—10.
- *Length of basal branches* (*from the base of the stem to the tip*).—About 9.0 cm.

*Internode length.*—0.4 cm to 1.0 cm.
*Diameter of branches (from midpoint).*—0.4 cm.
*Stem color.*—RHS 145D.
*Anthocyanin.*—Absent.
*Texture.*—Tomentose.

Leaves:
*Arrangement.*—Alternate.
*Length.*—5.0 cm to 7.0 cm.
*Width.*—2.0 cm to 2.7 cm.
*Shape.*—Elliptic.
*Apex.*—Acute.
*Base.*—Attenuate.
*Margin.*—Entire.
*Immature leaf color.*—Upper surface: RHS N137D. Lower surface: RHS 146B.
*Mature leaf color.*—Upper surface: RHS N137B. Lower surface: RHS 146B.
*Texture.*—Upper and lower surfaces: Tomentose.
*Venation pattern.*—Arcuate.
*Venation color.*—Upper surface: RHS N137B. Lower surface: RHS 145A.
*Petioles.*—Length: About 1.0 cm. Diameter: 0.4 cm. Color: RHS 145B. Texture: Tomentose.

Flower bud:
*Shape.*—Irregular oblong.
*Length.*—4.5 cm.
*Diameter.*—0.7 cm.
*Color at tight bud.*—RHS 145B at the base and RHS 150C at the top.
*Texture.*—Slightly pubescent.

Inflorescence:
*Blooming habit (flowering season).*—Permanent flowering during summertime.
*Inflorescence type.*—Cymose.
*Number of flowers per node.*—1.
*Lastingness of individual blooms on the plant.*—About one week.
*Fragrance.*—Absent.
*Flowers.*—Arrangement: Composed of 5 petals fused at the base. Diameter (flower face): 6.0 cm. Depth (total length of flower): 6.0 cm. Throat/Funnel: Length: 3.3 cm. Diameter (at opening): 1.5 cm. Texture: Inner and outer surfaces: Smooth, glabrous. Color: Inner surface: RHS 7A. Outer surface: RHS 150C. Petals: Color, mature flower (fully opened): Upper surface: Margin color of RHS 4D with veins of RHS 7A to RHS 7B (strong vein color provides the main color of the flower). Lower surface: RHS 4A. Apex: Mucronate. Base: Fused. Shape: Fused in a funnel. Margin: Entire. Strength of waviness: Weak. Degree of lobation: Weak.
*Calyx arrangement.*—Actinomorphic, composed of 5 sepals. Sepals: Color: Upper surface: RHS 137A. Lower surface: RHS 137C. Length: 1.7 cm to 2.0 cm. Width: 0.4 cm. Shape: Narrowly oblong. Apex: Acute. Base: Attenuate. Margin: Entire. Texture: Upper and lower surface: Pubescent.
*Pedicels.*—Color: RHS 144A. Length: 3.8 cm. Diameter: 0.2 cm. Texture: Pubescent.

Reproductive organs:
*Stamens.*—Quantity: 5. Shape: Needle like with elliptic head. Filament: Length: 1.3 cm. Diameter: 0.05 cm. Color: RHS 2D. Anther: Shape: Elliptic-oblong. Color: RHS 8B. Length: 0.2 cm. Diameter: 0.15 cm. Pollen: Color: RHS 11B. Amount: Abundant.
*Pistils.*—Quantity per flower: 1. Length: 2.7 cm. Stigma color: RHS 143A. Style color: RHS 145A.

Fruit and seed set: None observed.
Disease and pest insect resistance: None observed.

COMPARISON WITH PARENTAL LINES AND KNOWN VARIETY

'KLEPH15261' is a distinct variety of *petunia*. 'KLEPH15261' is distinguished from its parents as described in Table 1:

TABLE 1

Comparison with Parental Lines

| Trait | Variety 'KLEPH15261' | Female parent 'PH-2011-2754' | Male Parent 'PH-2009-1258' |
|---|---|---|---|
| Flower color | More uniform corolla color than the parental lines | Darker color than 'KLEPH15261' | Lighter margin than 'KLEPH15261' with a yellow center |
| Earliness | About two weeks earlier than 'PH-2009-1258' | | About two weeks later than 'KLEPH15261' |

'KLEPH15261' is most similar to the commercial *petunia* plant named Sunshine Ray (patent status unknown). Differences between the two varieties are described in Table 2:

TABLE 2

Comparison with Similar Variety

| Characteristic | Variety 'KLEPH15261' | Commercial line Sunshine Ray |
|---|---|---|
| Flower color | Yellow face and margin | Lighter margin and stronger vein center than 'KLEPH15261' |

We claim:

1. A new and distinct variety of *petunia* plant named 'KLEPH15261' as illustrated and described herein.

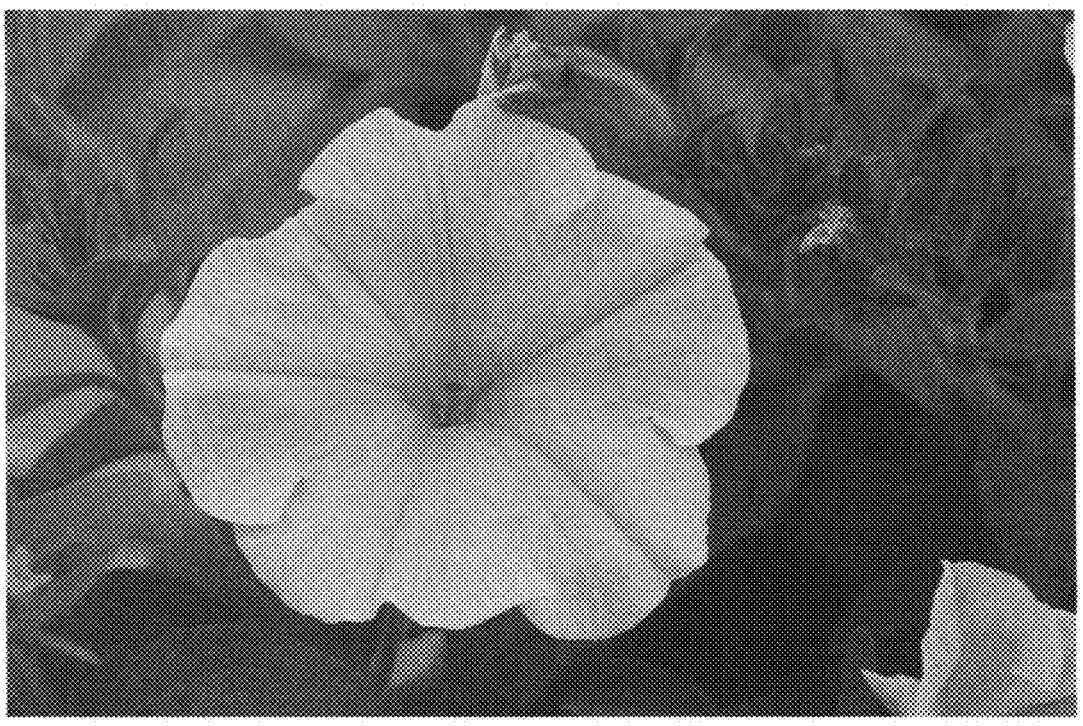

* * * * *